United States Patent
Kawano

(10) Patent No.: US 10,129,480 B2
(45) Date of Patent: Nov. 13, 2018

(54) SPECIMEN OBSERVATION DEVICE

(71) Applicant: OLYMPUS CORPORATION, Shibuya-ku, Tokyo (JP)

(72) Inventor: Yoshihiro Kawano, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 27 days.

(21) Appl. No.: 14/754,404

(22) Filed: Jun. 29, 2015

(65) Prior Publication Data

US 2016/0014343 A1    Jan. 14, 2016

(30) Foreign Application Priority Data

Jul. 9, 2014   (JP) ................................ 2014-141518

(51) Int. Cl.
*H04N 5/232*  (2006.01)
*H04N 5/262*  (2006.01)
(Continued)

(52) U.S. Cl.
CPC ....... *H04N 5/23293* (2013.01); *G02B 21/367* (2013.01); *G06F 3/041* (2013.01);
(Continued)

(58) Field of Classification Search
None
See application file for complete search history.

(56) References Cited

U.S. PATENT DOCUMENTS

| 5,428,690 A | 6/1995 | Bacus et al. |
| 2005/0181774 A1* | 8/2005 | Miyata .............. H04M 1/27455 455/414.1 |

(Continued)

FOREIGN PATENT DOCUMENTS

| EP | 557871 A2 | 9/1993 |
| JP | 2007298444 A | 11/2007 |

(Continued)

OTHER PUBLICATIONS

Extended European Search Report dated Nov. 9, 2015, issued in counterpart European Application No. 15175620.2.

(Continued)

*Primary Examiner* — Matthew Yeung
(74) *Attorney, Agent, or Firm* — Holtz, Holtz & Volek PC

(57) ABSTRACT

It is possible to readily observe pathology specimens without spending much time and suspected pathology specimens in detail. A specimen observation device comprises an image capturing unit acquiring a partial image representing at least a part of one of multiple pathology specimens mounted on an accommodating section and a whole image of the multiple pathology specimens mounted on the accommodating section; an input unit inputting identification information of the accommodating section; a display unit displaying an enlarged version of the partial image acquired by the image capturing unit); an image designating unit designating the partial image displayed on the display unit; and a storage unit storing the identification information input via the input unit and a position of the partial image designated via the image designating unit in relation to the whole image such that the position and the identification information are associated with the whole image.

15 Claims, 5 Drawing Sheets

(51) Int. Cl.
*G06F 3/041* (2006.01)
*G02B 21/36* (2006.01)
*G01N 35/00* (2006.01)

(52) U.S. Cl.
CPC ..... *H04N 5/2628* (2013.01); *G01N 35/00029* (2013.01); *G01N 35/00732* (2013.01); *G02B 21/365* (2013.01)

(56) References Cited

U.S. PATENT DOCUMENTS

| | | | |
|---|---|---|---|
| 2006/0075362 A1* | 4/2006 | Moteki | H04N 1/00442 715/838 |
| 2009/0087074 A1* | 4/2009 | Wong | G06K 9/00147 382/133 |
| 2014/0184778 A1 | 7/2014 | Takayama | |
| 2015/0086971 A1 | 3/2015 | Botma et al. | |
| 2016/0139387 A1* | 5/2016 | Virk | G02B 21/002 348/79 |

FOREIGN PATENT DOCUMENTS

| | | |
|---|---|---|
| JP | 2011047695 A | 3/2011 |
| JP | 2014056192 A | 3/2014 |
| JP | 2015132550 A | 7/2015 |
| WO | 2013147610 A2 | 10/2013 |

OTHER PUBLICATIONS

"TOCO", CARLO Inc., a product information webpage (URL: http://www.claro-inc.jp/product/toco) retrieved online by an Internet search conducted on May 21, 2014.

Japanese Office Action dated Jun. 5, 2018 (and an English translation thereof) issued in counterpart Japanese Application No. 2014-141518.

* cited by examiner

SPECIMEN OBSERVATION DEVICE

CROSS-REFERENCE TO RELATED APPLICATIONS

This application is based on Japanese Patent Application No. 2014-141518, the contents of which are incorporated herein by reference.

TECHNICAL FIELD

The present invention relates to specimen observation devices.

BACKGROUND ART

In the related art, pathology specimens are observed in order to diagnose pathological conditions of cells themselves by examining the sizes of the cell nuclei, cell heteromorphism, etc. or in order to diagnose whether or not the tissue of the specimen as a whole has developed cancer by examining the conditions of multiple cells or intercellular substances. In the case where tissue is to be diagnosed, the whole slide specimen is observed to check whether or not any abnormal shape is present.

When pathology specimens are supplied, usually, multiple (e.g., 24) specimens are mounted on a slide tray, which is an accommodating section in the shape of a single sheet, and the observer has to observe all the pathology specimens. There are known devices for acquiring images of multiple pathology specimens mounted on a slide tray (e.g., see Non Patent Literature 1).

CITATION LIST

Non Patent Literature

{NPL 1}
"TOCO", CLARO Inc., a product information webpage (URL: http://www.claro-inc.jp/product/toco) retrieved online by an Internet search conducted on May 21, 2014.

SUMMARY OF INVENTION

Such devices are used to acquire virtual slide images of the individual pathology specimens mounted on the slide tray. It is necessary to spend an enormous amount of time to acquire virtual slide images even for pathology specimens that can be apparently judged as involving no problem by a simple observation.

The present invention provides a specimen observation device with which it is possible to readily observe pathology specimens without spending much time and to readily observe suspected pathology specimens in detail.

The present invention, in one aspect thereof, provides a specimen observation device including an image capturing unit that acquires a partial image representing at least a part of one of multiple pathology specimens mounted on an accommodating section and a whole image of the multiple pathology specimens mounted on the accommodating section; an input unit for inputting identification information of the accommodating section; a display unit that displays an enlarged version of the partial image acquired by the image capturing unit; an image designating unit for designating the partial image displayed on the display unit; and a storage unit that stores the identification information input via the input unit and a position of the partial image designated via the image designating unit in relation to the whole image such that the position and the identification information are associated with the whole image.

In the above aspect, the input unit may be a reading unit that reads the identification information attached to the accommodating section.

In the above aspect, the identification information may be recorded on a surface of the accommodating section in a form of a barcode.

In the above aspect, the input unit may read the identification information from the barcode included in the whole image acquired by the image capturing unit.

In the above aspect, the image designating unit may be a touchscreen sensor provided on the display unit.

DESCRIPTION OF EMBODIMENTS

A specimen observation device 1 according to a first embodiment of the present invention will be described below with reference to the drawings.

Figure 1:
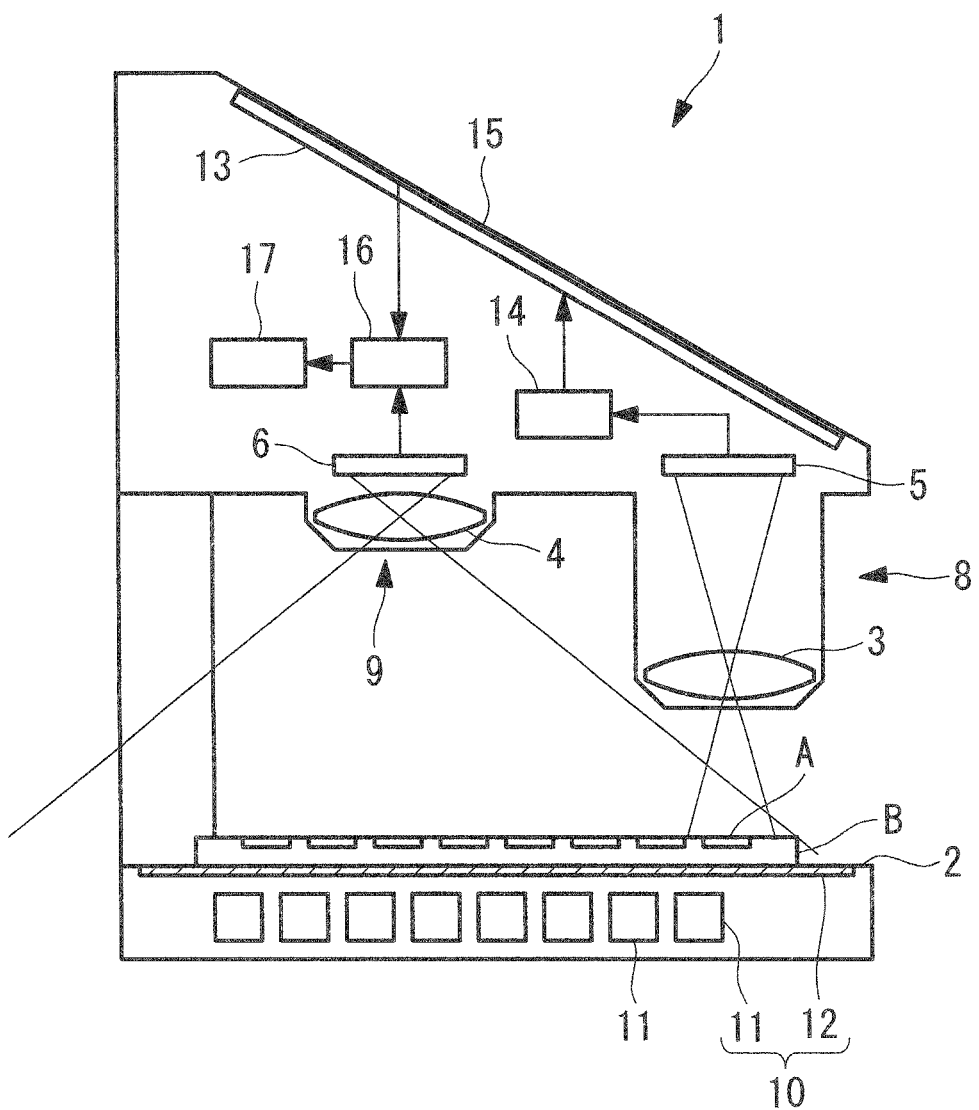
FIG. 1 is a vertical sectional view showing a specimen observation device according to an embodiment of the present invention.

As shown in FIG. 1, the specimen observation device 1 according to this embodiment includes a stage 2 for placing thereon an accommodating section (hereinafter referred to as a slide tray) B having mounted thereon multiple slides A containing pathology specimens and arrayed in a matrix, two objective lenses 3 and 4 provided above the stage 2 with a gap therebetween, and two image capturing devices 5 and 6 that capture light collected by the respective objective lenses 3 and 4.

Figure 2:
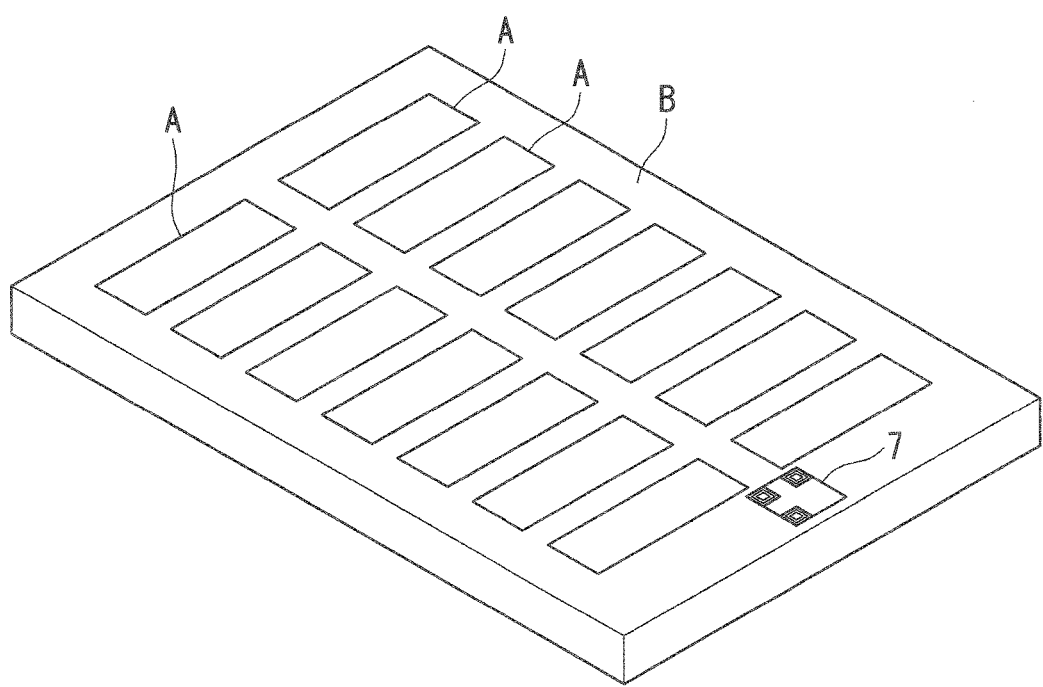
FIG. 2 is a perspective view showing an example of a slide tray supporting pathology specimens in the specimen observation device shown in FIG. 1.

As shown in FIG. 2, the slide tray B is a sheet-shaped unit having multiple recesses for individually holding multiple slides A. The slide tray B is made of a light-transmitting material or has an opening (not shown) through which light can be transmitted. Furthermore, on a portion of the surface thereof, the slide tray has a barcode 7 containing identification information that is unique to each slide tray B.

The objective lens 3 and the image capturing device 5 constitute a first image capturing unit 8, which has a field of view that makes it possible to acquire a partial image representing at least a part of the pathology specimen on each of the slides A.

The other objective lens 4 and the other image capturing device 6 constitute a second image capturing unit 9, which has a field of view that makes it possible to acquire a whole image of the whole slide tray B having mounted thereon the multiple slides A.

The stage 2 is provided with an illuminating device 10. In the illuminating device 10, light sources 11 are covered from above with a milky-white (opal-glass) X-ray film viewer 12, which makes it possible to uniformly illuminate the whole slide tray B mounted on the stage 2 from under the slide tray B.

Furthermore, the specimen observation device 1 according to this embodiment includes a monitor (display unit) 13 that displays an enlarged version of the partial image acquired by the first image capturing unit 8. Specifically, the objective lens 3 has a magnification of about two, so that it is possible to acquire a partial image in which a pathology specimen is optically enlarged by two. Furthermore, the partial image can be enlarged by a first image processing unit 14 by a display magnification, and the resulting enlarged image is displayed on the monitor 13. This makes it possible for an observer to check, on the monitor 13, whether a lesion is present or not more easily and accurately compared with the case where the observer visually inspects the pathology specimen.

On the screen of the monitor 13, a touchscreen sensor 15 is provided. The touchscreen sensor 15 is used to designate the displayed partial image itself or a partial region in the partial image. That is, the observer can touch the touchscreen sensor 15 so as to identify a displayed lesion while viewing the partial image displayed on the monitor 13 to designate (assign a "C" mark to) the partial image itself or the position of a partial region in the partial image.

Furthermore, the specimen observation device 1 according to this embodiment includes a second image processing unit 16 that processes the whole image acquired by the second image capturing unit 9 and a storage unit 17 that stores information generated by the second image processing unit 16.

The second image processing unit 16 processes the whole image to read identification information from the barcode 7 and to associate the read identification information, as well as the partial image or the position of the partial region designated by the touchscreen sensor 15, with the whole image.

That is, since the first image capturing unit 8 and the second image capturing unit 9 are provided in a fixed positional relationship relative to each other, the position of the partial image acquired by the first image capturing unit 8 in the whole image acquired by the second image capturing unit 9 is known.

Therefore, when the partial image itself or a partial region thereof is designated by using the touchscreen sensor 15, it is possible to readily identify the designated partial image or the position of the designated partial region.

The storage unit 17 is a computer-readable storage medium, such as a semiconductor memory, a magnetic disk, or a magneto-optical disk, provided in a personal computer, a server, etc.

Now, the operation of the thus-configured specimen observation device 1 according to this embodiment will be described below.

In order to observe pathology specimens by using the specimen observation device 1 according to this embodiment, the slide tray B with multiple slides A mounted thereon is placed on the stage 2.

Then, the whole slide tray B is uniformly illuminated by light emitted from the illuminating device 10, and images are captured by the first image capturing unit 8 and the second image capturing unit 9. Since the whole slide tray B is located in the field of view of the second image capturing unit 9, it is possible to acquire the whole image of the slide tray B with the multiple slides A mounted thereon. After the whole image is acquired, identification information is read from the image of the barcode 7 included in the whole image by the operation of the second image processing unit 16. The identification information that has been read is stored in the storage unit 17 in association with the whole image.

Meanwhile, the first image capturing unit 8 captures a partial image of one of the slides A mounted on the slide tray B, and the acquired partial image is enlarged, and the enlarged image is displayed on the monitor 13. The observer can shift the image capturing region of the first image capturing unit 8 by manually moving the slide tray B on the stage 2 in the horizontal direction to successively switch the partial image that is displayed on the monitor 13. Since the positions of the first image capturing unit 8 and the second image capturing unit 9 relative to each other are fixed, the position of the slide A represented in the partial image displayed on the monitor 13, in relation to the whole image, is known.

Figure 3:
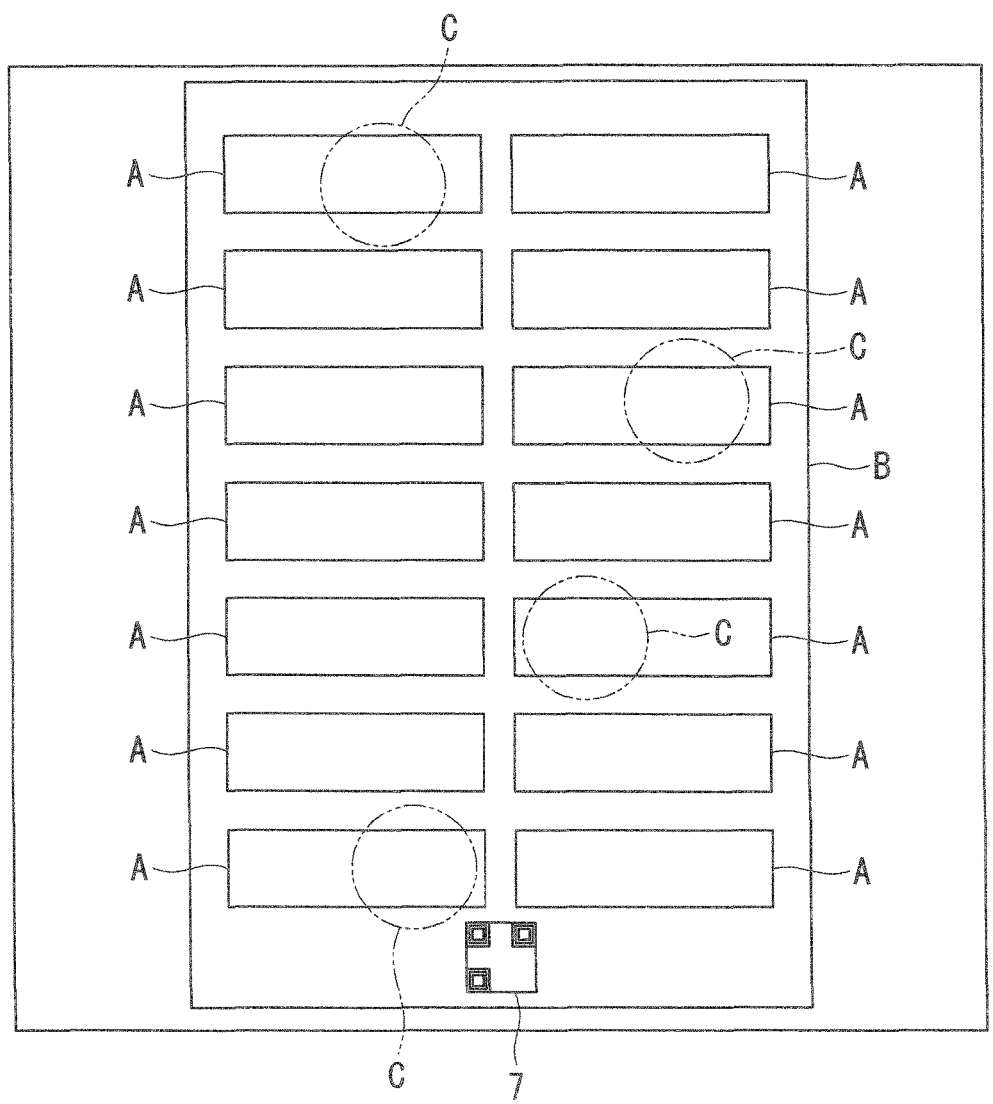
FIG. 3 is an illustration showing an example of an image that is stored in a storage unit, in which marks are assigned to a whole image acquired by the specimen observation device shown in FIG. 1.

Then, the observer observes the enlarged partial image displayed on the monitor 13 while moving the slide tray B. In the case where there is any region suspected of being a lesion, the observer touches the corresponding region on the monitor 13. Then, the partial image or the position of the region in the partial image designated by using the touchscreen sensor 15 is stored in the storage unit 17 in association with the whole image of the slide tray B by the second image processing unit 16, as shown in FIG. 3. The observer observes enlarged images of all the slides A by moving the slide tray B, and directly designates partial images or regions on the monitor 13 by using the touchscreen sensor 15. All these partial images and regions are stored in the storage unit 17 in association with the corresponding whole images.

Thus, by observing low-magnification enlarged images of the multiple slides A on a single slide tray B and then reading information stored in the storage unit 17, the observer can readily check which slides A on the slide tray B contained regions suspected of being lesions. For slides A containing pathology specimens including such regions suspected of being lesions, the observer can further conduct detailed observation using a high-magnification microscope.

For example, even in the case where the high-magnification microscope is located at a remote place, if the storage unit 17 is connected via a network (not shown) to a server installed in the vicinity of the high-magnification microscope, by reading the barcode 7 of the slide tray B, transmitted to the server, it is possible to readily check the whole images as well as the pathology specimens to which "C" marks have been assigned as suspected lesions, stored in the storage unit 17 in association with the identification information. Thus, it is possible to extract the slides A containing the pathology specimens having "C" marks assigned thereto from the slide tray B and to conduct detailed observation.

As described above, with the specimen observation device 1 according to this embodiment, it is possible to quickly observe the multiple slides A mounted on the slide tray B at a low magnification and to store, together with the identification information, the whole images of the slides A containing suspected lesions, in which the suspected lesions are indicated by "C" marks. Thus, there is no need to spend time to acquire virtual slide images for all the slides A as before. Accordingly, an advantage is afforded in that it is possible to readily observe pathology specimens in a short time and to readily observe suspected pathology specimens in detail.

Although identification information is read from the barcode 7 by processing a whole image acquired by the second image capturing unit 9 in the embodiment described above, alternatively, a barcode reader may be provided separately. Furthermore, as the input unit for inputting identification information, an input unit that enables manual input, such as a keyboard, may be adopted. The barcode 7 may be one-dimensional or two-dimensional, and other types of identification sign may be used instead of the barcode 7.

Furthermore, although the slide tray B is manually moved in the horizontal direction on the stage 2 in the embodiment described above, alternatively, the stage 2 may be automatically or semi-automatically moved in the horizontal direction, while fixing the slide tray B on the stage 2. This makes it possible to observe all the slides A on the slide tray B without missing any.

Figure 4:
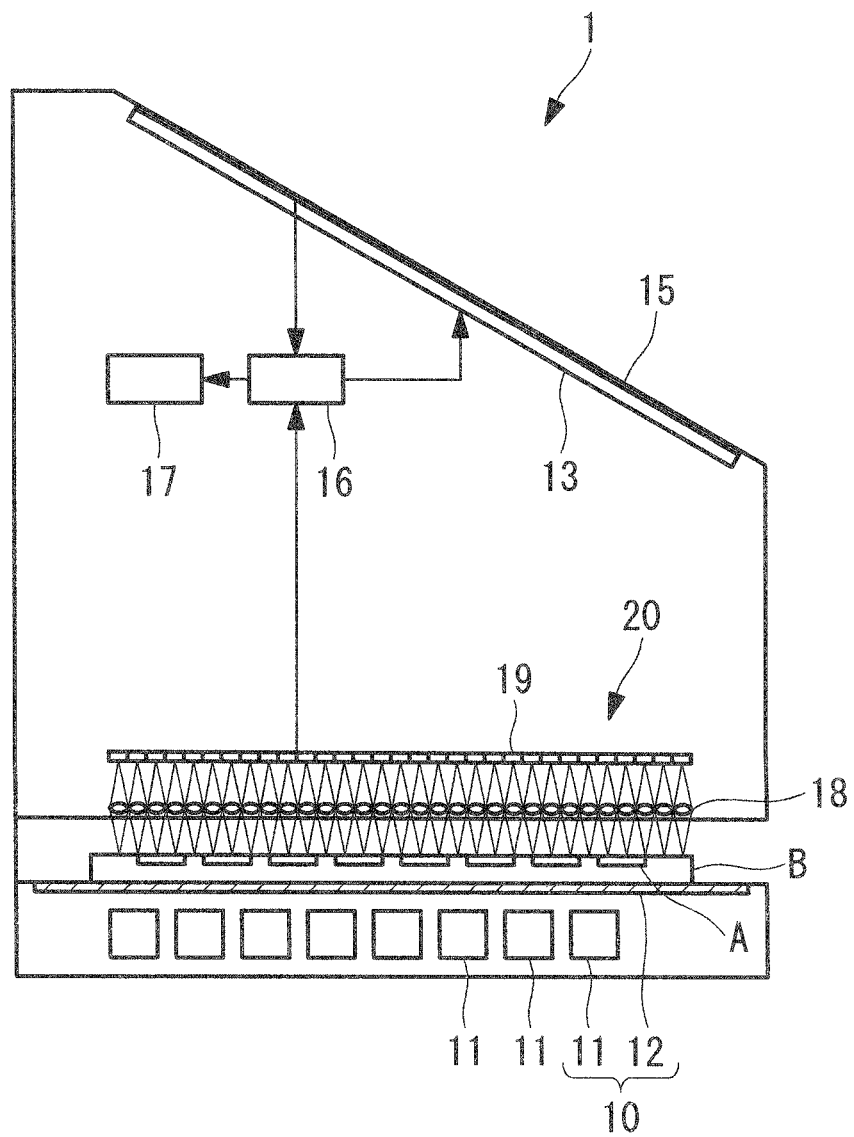
FIG. 4 is a vertical sectional view showing a modification of the specimen observation device shown in FIG. 1.

Furthermore, although partial images and a whole image are acquired by two image capturing units in the embodiment described above, namely, the first image capturing unit 8 and the second image capturing unit 9, alternatively, a single image capturing unit 20 that can acquire a whole image may be configured. As shown in FIG. 4, the image capturing unit 20 is implemented by a microlens array formed of multiple microlenses 18 arrayed horizontally with gaps therebetween above the stage 2 and multiple imaging devices 19, such as CODs or CMOSs, provided further above the microlens array. The pixel pitch of the CCDs may be about 5 µm, whereas the pixel pitch of the CMOSs may be 1 to 2 µm, which makes it possible to acquire a whole image with high precision. Thus, even if partial images corresponding to individual slides A are extracted from the whole image, it is possible to observe enlarged images with high precision.

Figure 5:
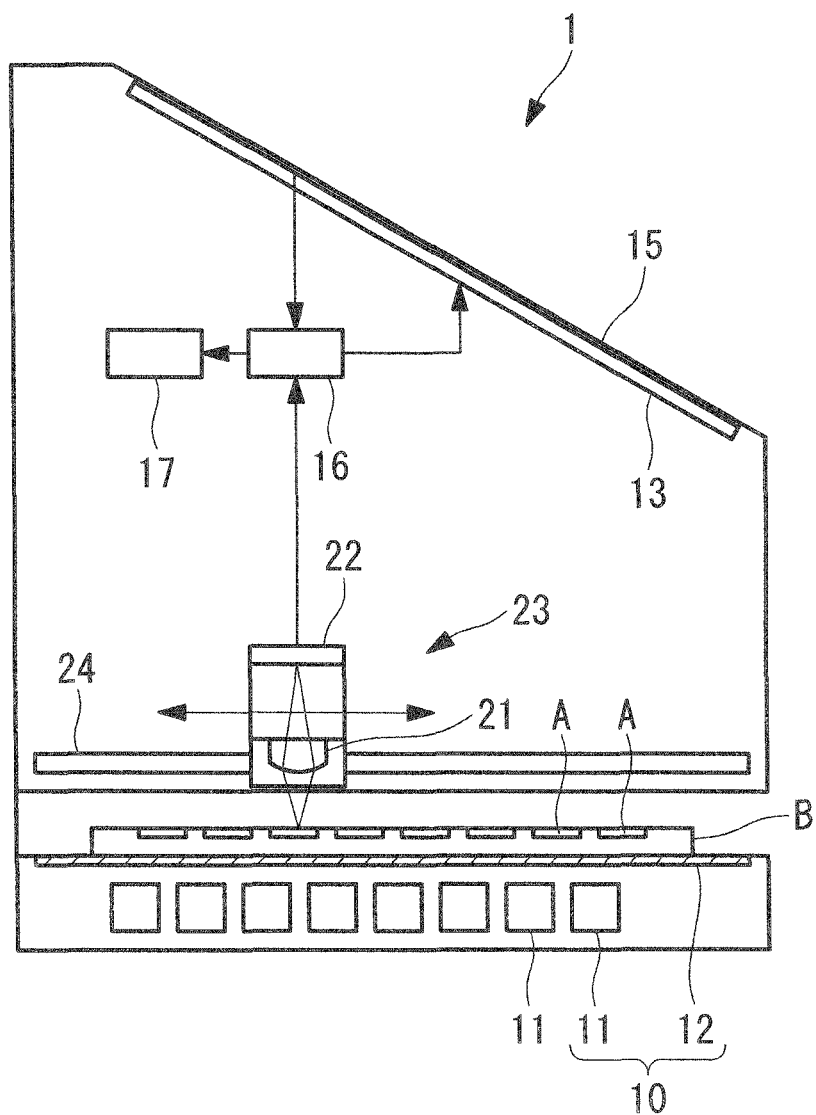
FIG. 5 is a vertical sectional view showing another modification of the specimen observation device shown in FIG. 1.

Alternatively, as shown in FIG. 5, an image capturing unit 23 that acquires a two-dimensional whole image by horizontally moving a cylindrical lens 21 and a line sensor 22 provided above the slide tray B may be adopted. In the figure, the reference sign 24 denotes a guide rail that supports the image capturing unit 23 such that the image capturing unit 23 can be moved horizontally. This also makes it possible to acquire a whole image with high precision, to extract partial images with high precision corresponding to the individual slides A from the whole image, and to observe enlarged images.

Furthermore, although identification information is read from the barcode 7 attached to the slide tray B by processing the whole image acquired by the second image capturing unit 9 in the embodiment described above, the second image processing unit 16 may process the whole image, read the identification information of each of the slides A from the barcode (not shown) attached thereto, and store the identification information in the storage unit 17 in association with a macro image of the slide A. This makes it possible to determine whether or not detailed observation is needed from the identification information of the slide A even after the slide A is removed from the slide tray B.

According to the above embodiment, a following aspect can be introduced.

The present invention, in one aspect thereof, provides a specimen observation device including an image capturing unit that acquires a partial image representing at least a part of one of multiple pathology specimens mounted on an accommodating section and a whole image of the multiple pathology specimens mounted on the accommodating section; an input unit for inputting identification information of the accommodating section; a display unit that displays an enlarged version of the partial image acquired by the image capturing unit; an image designating unit for designating the partial image displayed on the display unit; and a storage unit that stores the identification information input via the input unit and a position of the partial image designated via the image designating unit in relation to the whole image such that the position and the identification information are associated with the whole image.

According to this aspect, the image capturing unit acquires a whole image of the accommodating section having multiple pathology specimens mounted thereon, and also acquires a partial image of at least a part of one of the pathology specimens. The partial image is enlarged, and the enlarged partial image is displayed on the display unit. An observer can readily determine whether a lesion is present or not by checking the enlarged image of the pathology specimen, displayed on the display unit.

Then, in the case where there is no lesion, it is possible to move the accommodating section relative to the image capturing unit, thus readily switching to and displaying on the display unit another pathology specimen located at a different position. On the other hand, in the case where there is any suspected lesion, it is possible to designate, via the image designating unit, the partial image that is currently displayed on the display unit. Furthermore, it is possible to input the identification information of the accommodating section via the input unit.

Thus, when the partial image is designated, the position of the designated partial image in relation to the whole image and the identification information input via the input unit are stored in the storage unit in association with the whole image. Accordingly, by reading the stored information using the identification information as a key, it is possible to readily determine pathology specimens for which detailed observation is needed among the pathology specimens mounted on the accommodating section.

In the above aspect, the input unit may be a reading unit that reads the identification information attached to the accommodating section.

In this case, since the identification information attached to the accommodating section is read by the operation of the reading unit, it is possible to readily associate the identification information with the whole image without performing a special reading operation.

In the above aspect, the identification information may be recorded on a surface of the accommodating section in a form of a barcode.

In the above aspect, the input unit may read the identification information from the barcode included in the whole image acquired by the image capturing unit.

In this case, the image capturing unit also functions as a reading unit, rather than providing a special reading unit, and it is possible to read identification information in the form of a barcode by acquiring a whole image.

In the above aspect, the image designating unit may be a touchscreen sensor provided on the display unit.

In this case, in the case where there is any suspected lesion in the enlarged partial image of the pathology specimen, displayed on the display unit, it is possible to readily designate the position of the lesion in the whole image by directly touching the corresponding region on the display unit.

According to the above aspect, an advantage is afforded in that it is possible to readily observe pathology specimens without spending much time and to readily observe suspected pathology specimens in detail.

REFERENCE SIGNS LIST

A slides (pathology specimens)
B slide tray (accommodating section)
1 specimen observation device
7 barcode 8 first image capturing unit (image capturing unit)
9 second image capturing unit (image capturing unit)
13 monitor (display unit)
15 touchscreen sensor (image designating unit)
16 second image processing unit (input unit)
17 storage unit
20, 23 image capturing units

The invention claimed is:

1. A specimen observation device comprising:
an image capturing device that acquires (i) a whole image of multiple slides mounted on an accommodating section, each slide containing at least one pathology specimen, and (ii) a partial image representing at least a part of one of the pathology specimens of the multiple slides mounted on the accommodating section;
a first input device that inputs identification information of at least one of the accommodating section and the pathology specimens;
a second input device comprising a display and a touchscreen sensor provided on the display, the second input device designating a position of at least one lesion in the pathology specimens based on a user operation input on the touchscreen sensor while an enlarged partial image is being displayed on the display; and
a storage that stores the identification information input via the first input device and the position of the at least one lesion designated via the second input device in relation to the whole image such that the position and the identification information are associated with the whole image,
wherein, while the whole image is being displayed on the display, information indicating the position of the at least one lesion is displayed in a manner superimposed on the pathology specimens within the displayed whole image such that a position of the displayed information corresponds to a respective one of the slides in which the position of the at least one lesion has been designated by the second input device.

2. The specimen observation device according to claim 1, wherein the display displays the enlarged version of the partial image.

3. The specimen observation device according to claim 2, wherein the partial image represents a part of the whole image.

4. The specimen observation device according to claim 2, wherein the at least one lesion, the position of which is designated via the second input device, is at least one lesion included in the partial image.

5. The specimen observation device according to claim 1, wherein the first input device comprises a reading device that reads the identification information, the identification information being attached to the accommodating section.

6. The specimen observation device according to claim 5, wherein the identification information is a barcode recorded on a surface of the accommodating section.

7. The specimen observation device according to claim 5, wherein the identification information is a barcode included in the whole image acquired by the image capturing device.

8. The specimen observation device according to claim 1, wherein the image capturing device includes:
two objective lenses; and
two imaging devices that capture light collected by the respective objective lenses.

9. The specimen observation device according to claim 8, wherein:
one of the two objective lenses has a field of view that makes it possible to acquire a partial image representing at least a part of one of the pathology specimens,
the other one of the two objective lenses has a field of view that makes it possible to acquire a whole image of the accommodating section, and
a magnification of the one of the two objective lenses is higher than a magnification of the other one of the two objective lenses.

10. The specimen observation device according to claim 1, wherein the image capturing device includes a microlens array formed of multiple microlenses arrayed horizontally, and multiple imaging devices each of which comprises one of a CCD and a CMOS.

11. The specimen observation device according to claim 1, wherein the image capturing device includes a cylindrical lens and a line sensor, and
wherein the whole image is acquired by horizontally moving the image capturing device.

12. The specimen observation device according to claim 1, wherein the whole image is an image of the accommodating section on which the multiple slides are mounted.

13. The specimen observation device according to claim 12, wherein the image capturing device has a field of view that makes it possible to acquire the whole image of the accommodating section on which multiple slides are mounted.

14. The specimen observation device according to claim 1, wherein the storage is connected via a network to a server.

15. The specimen observation device according to claim 1, wherein the information indicating the position of the at least one lesion is a circular mark.

* * * * *